US00PP26086P3

(12) United States Plant Patent
Grosser

(10) Patent No.: US PP26,086 P3
(45) Date of Patent: Nov. 17, 2015

(54) MANDARIN TREE NAMED 'C4-15-19'

(50) Latin Name: *Citrus reticulata*
Varietal Denomination: C4-15-19

(71) Applicant: Florida Foundation Seed Producers, Inc., Marianna, FL (US)

(72) Inventor: Jude W. Grosser, Winter Haven, FL (US)

(73) Assignee: Florida Foundation Seed Producers, Inc., Marianna, FL (US)

( * ) Notice: Subject to any disclaimer, the term of this patent is extended or adjusted under 35 U.S.C. 154(b) by 90 days.

(21) Appl. No.: 13/987,563

(22) Filed: Aug. 7, 2013

(65) Prior Publication Data

US 2015/0047083 P1 Feb. 12, 2015

(51) Int. Cl.
*A01H 5/08* (2006.01)

(52) U.S. Cl.
USPC ..... Plt./202
CPC ..... *A01H 5/0806* (2013.01)

(58) Field of Classification Search
USPC ..... Plt./202
CPC ..... A01H 5/0806
See application file for complete search history.

(56) References Cited

U.S. PATENT DOCUMENTS

| | | | |
|---|---|---|---|
| PP21,224 | P2 | 8/2010 | Grosser et al. |
| PP21,356 | P3 | 10/2010 | Gmitter, Jr. et al. |
| PP21,535 | P2 | 11/2010 | Grosser et al. |
| 2013/0276180 | P1 | 10/2013 | Grosser |

OTHER PUBLICATIONS

Citrus, Apr. 2013.*
U.S. Appl. No. 13/987,609, filed Aug. 13, 2013, Grosser.
Grosser et al., "Highlights from the UF/IFAS/CREC Citrus Improvement Program," presentation at the Florida Citrus Show, Ft. Pierce, Florida, Jan. 19-20, 2011.

* cited by examiner

*Primary Examiner* — Keith Robinson
(74) *Attorney, Agent, or Firm* — Dentons US LLP

(57) ABSTRACT

An interploid cross (conventional breeding) of Sugar Belle® (patented as 'LB8-9', U.S. Plant Pat. No. 21,356) mandarin hybrid with a somatic hybrid of ['Nova' mandarin hybrid+ 'Succari' sweet orange], followed by embryo rescue, led to the recovery of the seedless triploid hybrid known as 'C4-15-19'. Trees of 'C4-15-19' are productive, producing an attractive peelable tangerine fruit with robust sweet flavor, maturing in October/November under Florida conditions. Fruit size is small-to-medium, and quite uniform.

7 Drawing Sheets

Latin name of the genus and species of the plant claimed: *Citrus reticulata.*
Variety denomination: 'C4-15-19'.

BACKGROUND OF THE INVENTION

The present invention relates to a new and distinct variety of mandarin tree named 'C4-15-19'. 'C4-15-19' is a triploid hybrid from an interploid cross of diploid monoembryonic 'Sugar Belle'®, patented as 'LB8-9' (U.S. Plant Pat. No. 21,356) tangelo (female parent) crossed with an allotetraploid somatic hybrid of 'Nova' mandarin hybrid (unpatented, Clementine×Orlando)+'Succari' sweet orange (*Citrus sinensis* L. Osbeck) (male parent, unpatented), obtained via embryo rescue. Two original trees exist in Lake Alfred, Fla., one of which is grafted to 'Carrizo' (unpatented) citrus rootstock, and the other of which is grafted to a somatic hybrid of sour orange+'Flying Dragon' (unpatented). 'C4-15-19' was first asexually reproduced in Lake Alfred, Fla. Trueness-to-type through asexual propagation was demonstrated by top-working (grafting) onto the somatic hybrid rootstock sour orange+'Carrizo', also located in Lake Alfred, Fla.

SUMMARY OF THE INVENTION

'C4-15-19' produces a 'Clementine'-sized, seedless, peelable tangerine-type fruit with high sugar content and a very sweet flavor. Fruit matures between October and November in Lake Alfred, Fla. (USDA Zone 9), depending on environmental factors. Fruit pigments well under typical Florida weather conditions (without cold-induction), both internally and externally. Fruit of 'C4-15-19' should be clipped to avoid plugging, particularly with fruit harvested during the latter part of the harvest season. Initiation of peel removal is easy, and the top half of the fruit is generally much easier to peel than the bottom half. Peelability of 'C4-15-19' seems to improve during storage. The rind contains large oil glands, and pleasantly fragrant oil can be released during peeling, especially with recently harvested fruit. This characteristic is expected to diminish as the trees grow through juvenility. The original tree yielded approximately 1 to 1.5 boxes (90 lbs per box) of fruit in 2013 on a dwarf tree (5 feet in height).

'C4-15-19' has a unique fruit, and is not directly comparable to any commercial variety. 'C4-15-19' is also morphologically distinct from both parent varieties. The female parent, 'Sugar Belle'® ('LB8-9'), produces a larger, bell-shaped fruit that is much tangier, more difficult to peel, and is seedy. The pollen parent, 'Nova'+'Succari', produces a similar-shaped but larger fruit, some seeds, and has a smoother rind, poor internal color, and less pleasant and acidic flavor.

BRIEF DESCRIPTION OF THE DRAWINGS

'C4-15-19' is illustrated by the accompanying photographs, which show the tree's form, foliage and fruit. The color chart used for color designations was The R.H.S. Colour Chart by The Royal Horticultural Society in London, Second Edition, in association with the Flower Council of Holland. The colors shown are as true as can be reasonably obtained by conventional photographic procedures. The photographs are of a single tree approximately 6 years old.

FIG. 1—Shows a close-up of the mature fruit with the rind and cross-sectional view.

FIG. 2—Shows nearly mature fruits hanging on the tree.

FIG. 3—Shows a close-up of leaves and nearly mature fruits.

FIG. 4—Shows a close-up of the mature fruit.

FIG. 5—Shows the overall mature plant growth habit in late summer.

FIG. 6—Shows an additional close-up of the very mature fruit hanging on the tree.

FIG. 7—Shows view of mature fruit from top, bottom, side, and center-cut angles (photo taken in November 2012).

DETAILED BOTANICAL DESCRIPTION

Phenotypic Description of *Citrus reticulata* 'C4-15-19'

Figure 1:
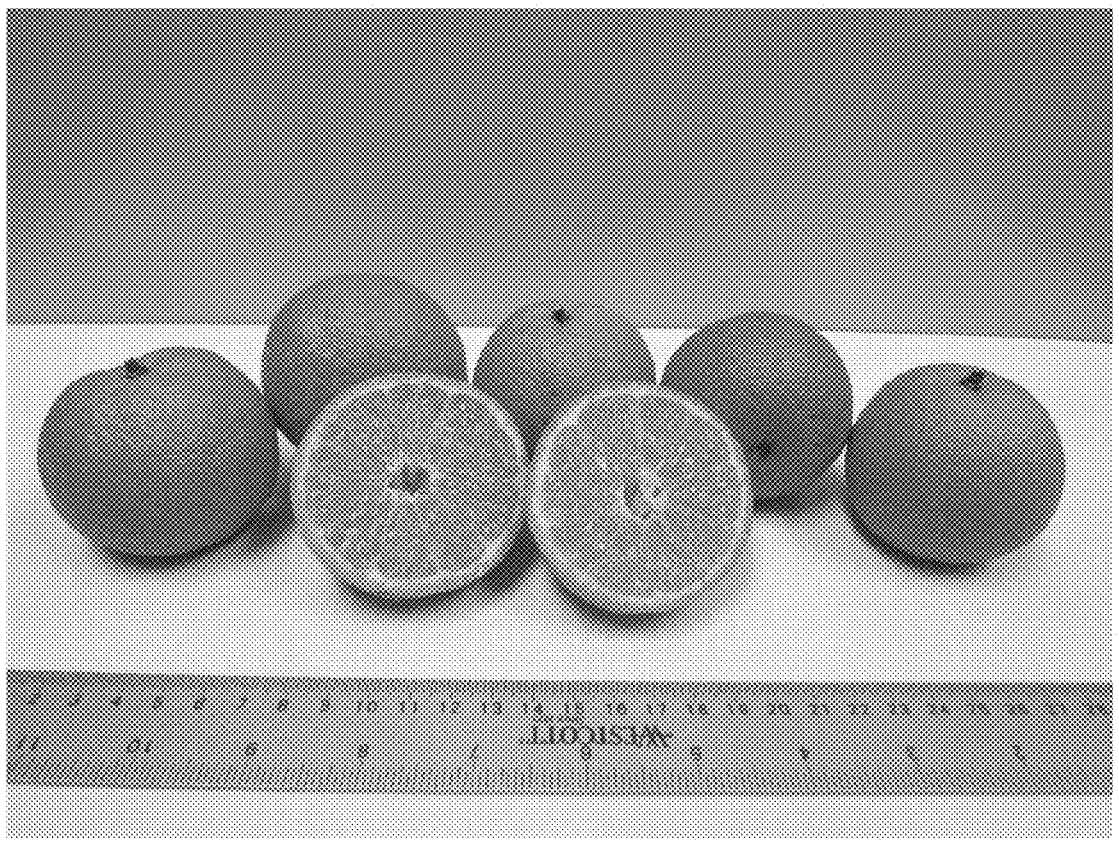
FIGS. 1, 2, and 3 were taken in the fall of 2012.
Figure 2:
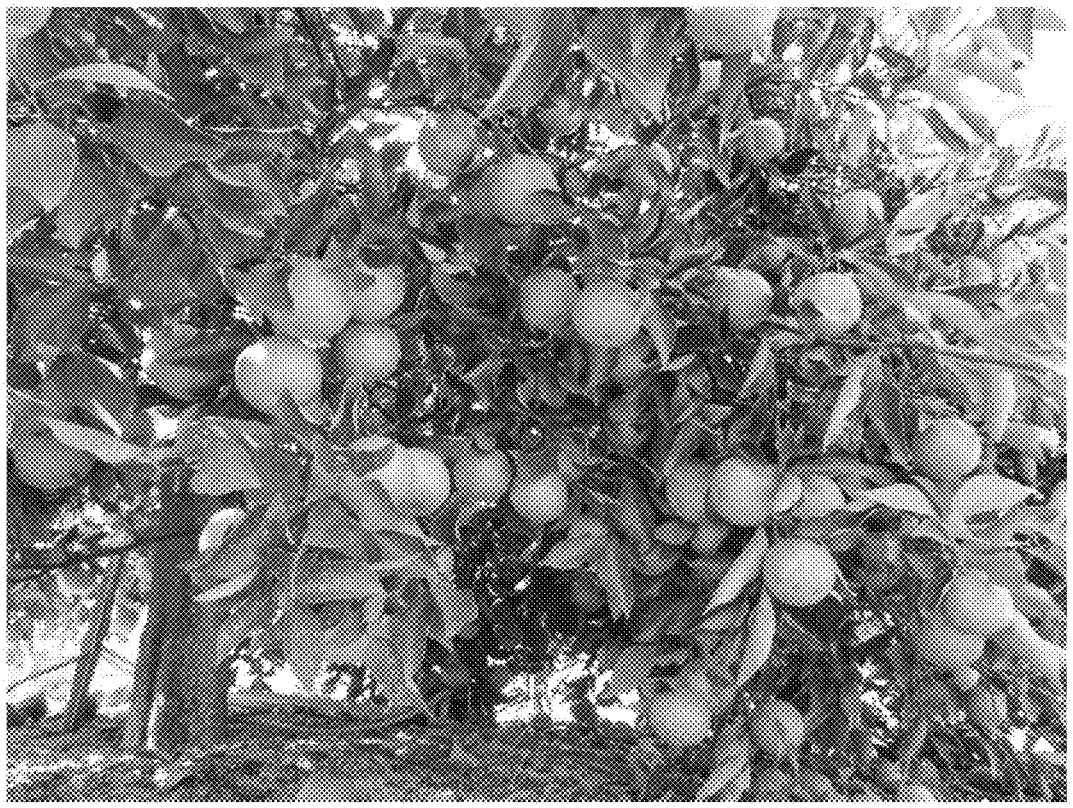
Figure 3:
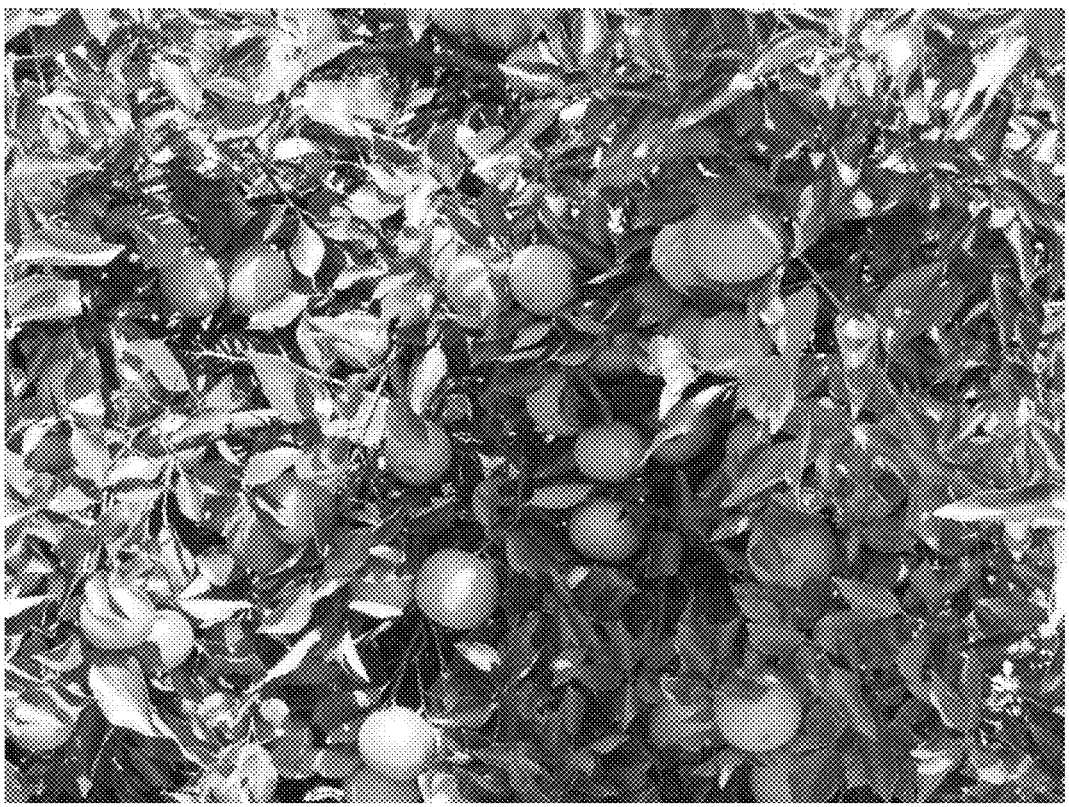
Figure 4:
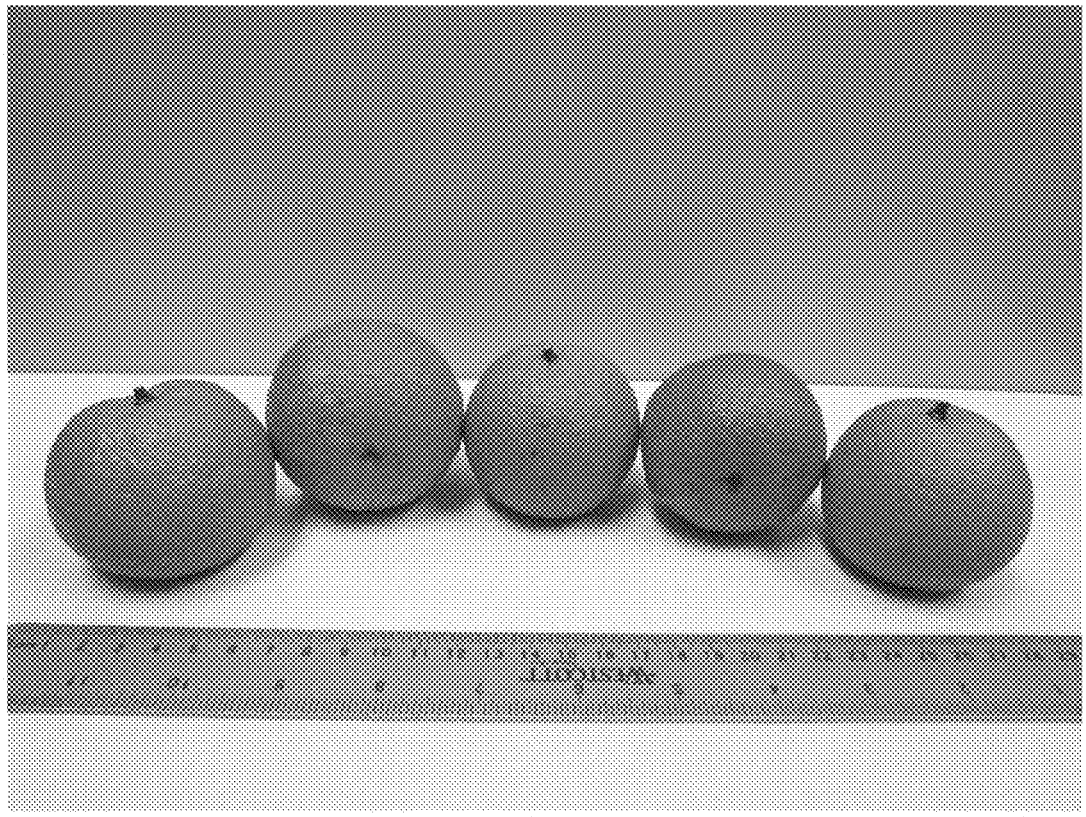
FIGS. 4, 5, 6, and 7 were taken during the early winter from the same tree.
Figure 5:
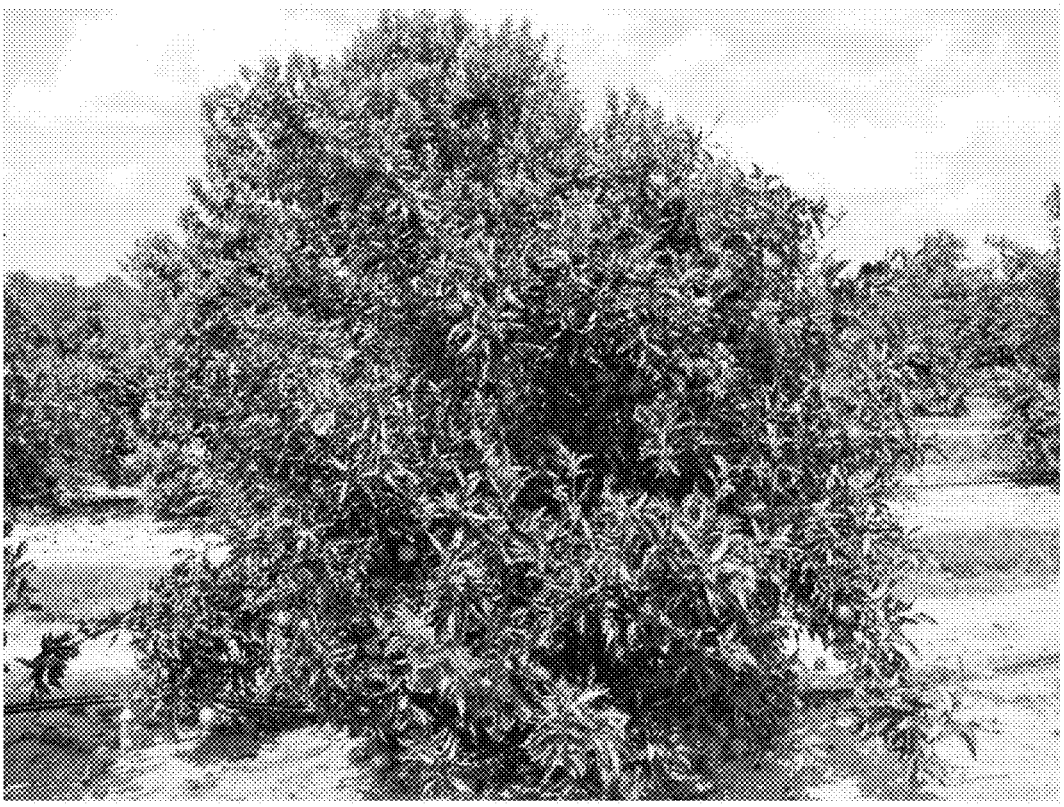
Figure 6:
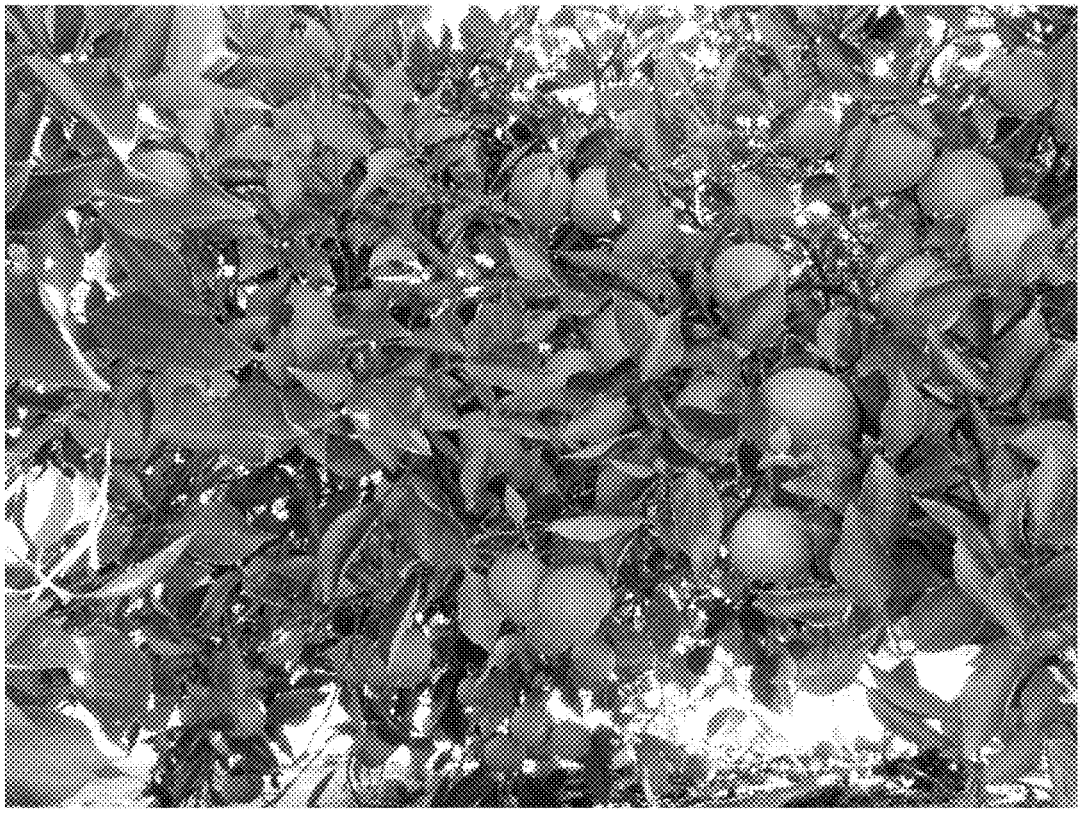
Figure 7:
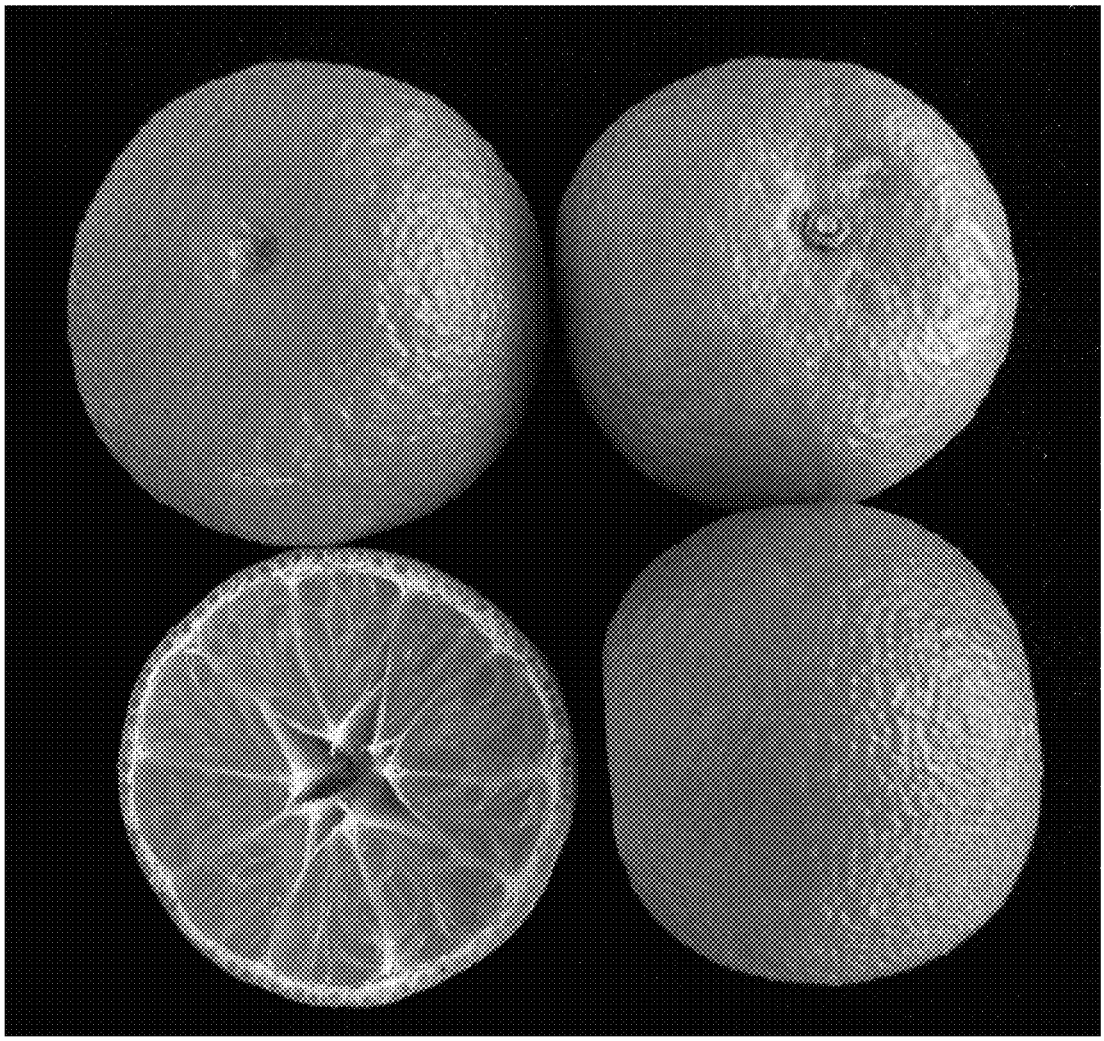

The following botanical description was taken of a tree approximately 4.5 years old.

Classification:

*Botanical.*—*Citrus reticulata* hybid×somatic hybrid of *C. reticulata* hybrid+*C. sinensis.*

*Common name.*—Mandarin hybrid or Tangerine.

Parentage:

*Female parent.*—'LB8-9' tangelo (Clementine×Minneola).

*Male parent.*—Somatic hybrid of 'Nova' mandarin hybrid (Clementine×Orlando)+'Succari' Sweet Orange (unpatented).

Tree:

*Ploidy.*—Triploid.

*Height.*—2.2 m.

*Tree spread.*—2.9 to 3.0 m.

*Vigor.*—Moderately vigorous.

*Density.*—Canopies are quite dense.

*Form.*—The tree has a rounded shape with many lateral and upright branches growing toward low angles. Branches with fruit exhibit drooping.

*Growth habit.*—Both upright and lateral growth with drooping branches.

Trunk:

*Trunk diameter.*—7.4 cm at 30 cm height above the ground.

*Trunk texture.*—Smooth.

*Trunk bark color.*—RHS N200A (brown); irregularly striated with RHS 198A (greyed-green).

Branches:

*Crotch angle.*—First crotch from 110- to 115-degree angle, middle crotch formed 65-degree angle.

*Branch length.*—Branch reaches 2.7 m from the first crotch to the tip of the branch.

*Branch texture.*—Relatively smooth, occasionally with small thorns or spines.

*Spines.*—Length: 27.7 to 38.8 mm on average. Diameter: 2.2 to 2.3 mm on average. Color: RHS 137C (green).

*Branch color* (*shoots from previous flush, hardened and* 4 to 5 mm in diameter).—RHS 138A (green).

Leaves:

*Size* (*lamina average*).—Length: 93.8 mm. Width: 57.4 mm. L/W ratio: 1.63.

*Thickness.*—Slightly thicker than regular and average when compare to commercial mandarin hybrids, ranging on average from 0.22 to 0.25 mm.

*Type.*—Simple.

*Shape.*—Elliptical.

*Apex.*—Retuse.

*Base.*—Acute to sub-obtuse.

*Margin.*—Entire and slightly undulate.

*Leaf blade.*—Appears to have weak blistering, with emargination present at the tip.

*Surface.*—Upper surface: Glabrous. Lower surface: Medium veins that are pinnately netted.

*Color.*—Upper surface (adaxial): RHS N137B (green). Lower surface (abaxial): RHS 138A (green).

*Petiole.*—Shape: Brevipetiolate (shorter than leaf lamina); junction between petiole and lamina is articulate. Width (petiole wing): Narrow. Shape (petiole wing): Obovate. Length: 16 to 19 mm. Width: 4 to 5.5 mm. Color: RHS N137B (green).

Flowers and flower buds:

*Type.*—Hermaphrodite.

*Bearing.*—Flowers grow from leaf axillaries and leaf terminals singly and in small clusters, with most single flowers growing from leaf terminals; each flower branch consists of 2-20 flowers.

*Flower diameter.*—Fully open flower with average diameter of 32 to 33 mm.

*Flower depth.*—Typical flower with average depth of 15.2 mm.

*Flower blooming period.*—First bloom: Observed Feb. 10, 2013. Full bloom: Observed Feb. 20, 2013.

*Flower bud.*—Length: Initial visible flower bud is 1.2 mm in length; mature flower bud is 11 mm in length. Diameter: Initial visible flower bud is 4 mm in diameter; mature flower bud is 7.2 mm in diameter. Shape: Initial visible flower bud has round ball shape; mature flower bud has elongated olive shape. Texture: Young flower bud has a very firm texture, fully mature flower bud appear to be medium firm and waxy. Color: RHS 142C (green) for initial visible flower bud; RHS 155C (white) for mature flower bud with RHS 1C (green-yellow) spots distributed at tip of the flower bud.

*Flower petals.*—Length: 15.3 mm. Width: 6.5 to 6.9 mm. Shape: Flat, spatula shaped. Apex shape: Smooth, acute shaped. Base shape: Even obtuse.

*Color.*—Upper surface: RHS 155C (white). Lower surface: RHS 155C (white) with RHS 1C (green-yellow) spots distributed toward to the petal apex. Margin: Smooth.

*Sepal.*—Number: 5 per flower. Shape: Delta shaped with acute angle at apex. Length: 2.5 mm. Width: 2.6 mm. Apex shape: Triangle shaped. Margin: Smooth.

*Color.*—Upper surface: RHS 145C (yellow-green). Lower surface: RHS 145C (yellow-green).

*Fragrance.*—Fragrant.

*Pedicel.*—Length: 3.5 to 3.8 mm. Diameter: 1.5 to 1.8 mm. Color: RHS 145A (yellow-green).

*Reproductive organs.*—Fertility: Appears self-fertile. Style Length: 12.9 to 13.2 mm. Stamen length: 11.8 to 12 mm. Anther length: 3.2 mm. Anther Width: 1.0 to 1.2 mm. Anther color: RHS 12C (yellow). Anther filament length: 9.5 to 9.6 mm. Pollen amount: Abundant. Pollen color: RHS 13A (yellow).

Fruit:

*Size*.—Uniform.

*Height*.—53.5 to 57.2 mm on average.

*Width*.—61 to 63.5 mm on average.

*Average weight* (*per individual fruit*).—108 g.

*Shape*.—Round.

*Shape* (*cross-section*).—Round.

*Broadest part of the fruit measured as fruit width at the middle of the fruit*.—61 to 63.5 mm on average.

*Color of fruit surface*.—RHS 21C (yellow-orange).

*Apex*.—Truncated.

*Apex cavity diameter*.—N/A.

*Presence of depression in fruit*.—Shallow depression at fruit apex.

*Base*.—Not necked.

*Base cavity diameter*.—4.5 to 4.8 mm.

*Constriction at stalk end*.—Medium strength constriction.

*Radial grooves*.—Most fruit have a smooth distal end, occasionally some fruits with weak radial grooves at distal end of the fruit.

*Naval opening*.—Not present.

*Fruit collar*.—Not present.

*Fruit areola*.—Not present.

*Harvesting*.—First harvest is usually around the 1st of October (based on season and rootstock); last harvest around is generally from mid-late November.

*Fruit stem* (*short stem connecting the fruit*).—Length: 5.0 mm. Diameter: 2.9 mm. Color: RHS 138A (green) with RHS 197C (greyed-orange) strip.

*Parthenocarpy of fruit*.—Parthenocarpic; self-incompatibility unknown.

Skin:

*Adherence*.—Adherence between albedo (mesocarp) and flesh (endocarp) is medium to weak, stronger adherence at basal end of fruit, easier to peel than 'Murcott' tangerine (unpatented), with less adherence than its female parent 'Sugar Belle'® (patented as 'LB8-9', U.S. Plant Pat. No. 21,356).

*Fruit rind strength*.—Fruit rind appears to be medium firm.

*Thickness*.—2.8 to 3.0 mm on average.

*Texture*.—Smooth.

*Color*.—Flavedo (epicarp): Ranges between RHS 21C (yellow-orange) to RHS 23C (yellow-orange) in October; RHS 24A (orange) to RHS 25N (reddish-orange) in November. Albedo (mesocarp): RHS 20C (yellow-orange).

*Stylar end*.—Closed.

*Rind oil cell density*.—88-92 oil cells/square cm.

*Oiliness of fruit rind*.—Appears to be medium-high, with more oil on fruit from juvenile trees.

Flesh:

*Number of segments*.—Average between 9 and 10 segments per fruit.

*Segment walls*.—Medium firm with sufficient strength to maintain integrity as separated.

*Juice*.—Abundant.

*Color*.—Uniformly RHS 23B (yellow-orange).

*Juice color*.—42.6 (November); RHS 25A (yellow-orange).

*Texture*.—Medium soft.

*Vesicles*.—Length: arranged from 11.0 to 12.5 mm on average. Diameter (thickness): 3.5 to 4.2 mm in average.

*Time of maturity of fruit for consumption*.—October through mid-December. Depends on environmental conditions, with external color becoming increasingly reddish/orange as season progresses.

*Eating quality* (*varies from season to season*).—2012 mid-November data.

*Soluble solids* (*average*).—14.4 Brix.

*Acidity* (*average*).—0.68%.

*Ratio*.—21.2.

Seeds: Seedless (seeds rarely found).

Resistance to disease: Alternaria (*Alternaria altemata*) and citrus scab (*Elsinoë fawcettii*) have not been observed in the trees or fruit currently grown. The original trees are growing in a block of trees heavily impacted by HLB (Huanglongbing or citrus greening). One of the original trees has been diagnosed with HLB, with symptoms being observed in the winter months (first observed in February, 2013); however, symptomatic branches died, and the remainder of the tree appears to be recovering. Under optimized nutrition, infected trees can maintain productivity of quality fruit. 'C4-15-19' exhibits better HLB tolerance than sweet orange, but less tolerance than female parent 'Sugar Belle'® ('LB8-9').

What is claimed is:

1. A new and distinct cultivar of mandarin tree as illustrated and described herein.

* * * * *